(12) United States Patent
Yazdi

(10) Patent No.: US 7,934,927 B2
(45) Date of Patent: May 3, 2011

(54) IMPACTED TOOTH APPLIANCE

(76) Inventor: Mohamadreza Yazdi, West Hills, CA (US)

( * ) Notice: Subject to any disclaimer, the term of this patent is extended or adjusted under 35 U.S.C. 154(b) by 271 days.

(21) Appl. No.: 12/006,770

(22) Filed: Jan. 7, 2008

(65) Prior Publication Data

US 2008/0254401 A1 Oct. 16, 2008

Related U.S. Application Data

(60) Provisional application No. 60/922,891, filed on Apr. 12, 2007.

(51) Int. Cl.
*A61C 3/00* (2006.01)
(52) U.S. Cl. .................. 433/18; 433/21; 433/24
(58) Field of Classification Search .......... 433/8, 9, 433/10, 13, 18, 19, 21, 24, 172–176
See application file for complete search history.

(56) References Cited

U.S. PATENT DOCUMENTS

| 5,588,838 | A | * | 12/1996 | Hansson et al. | ............... 433/173 |
| 5,921,774 | A | | 7/1999 | Kanomi et al. | |
| 6,354,834 | B2 | * | 3/2002 | Kanomi et al. | ................. 433/18 |
| 7,172,416 | B2 | | 2/2007 | Lin | |
| 2004/0152035 | A1 | * | 8/2004 | Bumann et al. | ................. 433/18 |
| 2007/0264607 | A1 | * | 11/2007 | Olavarria Landa | ............. 433/18 |

* cited by examiner

*Primary Examiner* — Cris L Rodriguez
*Assistant Examiner* — Eric Rosen
(74) *Attorney, Agent, or Firm* — Rodgers & Rodgers

(57) ABSTRACT

An impacted tooth appliance including a micropin bone anchor with a quadrilateral aperture formed therein, a rigid apertured ribbon secured to the impacted tooth by means of a rotatable bracket secured to the tooth, the ribbon pivoted on the bracket, and the ribbon and the micropin interconnected by means of spring-biased quadrilateral wire.

13 Claims, 2 Drawing Sheets

IMPACTED TOOTH APPLIANCE

The benefits under 35 U.S.C. 119 are claimed of provisional patent application 60/922,891 filed Apr. 12, 2007.

BACKGROUND OF THE INVENTION

The conventional technique for recovering a deeply impacted tooth is to bond a bracket with a gold chain attachment in order to anchor the impacted booth. Following this, it is required to level and align the remaining dentition in the arch to serve as an anchor unit against which the impacted tooth is leveraged. As a result, movement of the impacted tooth has to wait until the remainder of the arch is aligned sufficiently so it can accept a stiff archwire. Then, the tooth is tied to the main archwire and tugged on to force eruption of the impacted tooth. The most difficult aspect of bringing down an impacted tooth is maneuvering it into the oral cavity. Once this is achieved, many types of auxiliary archwires are utilized to guide the tooth into the proper position. All of these designs use the main archwire or a transpalatal arch as the anchor unit for the movement of the impacted tooth. The cuspid tooth is the most commonly impacted tooth; however, these arrangements are applicable to other impacted teeth such as the anterior teeth or premolars.

BRIEF SUMMARY OF THE INVENTION

According to this invention, the correction of the cuspid or other tooth is no longer tied to the leveling and alignment of the remainder of the arch. The unique feature of this system is in treating malocclusions that are complicated with the correction of malocclusions addressed independently of the impacted tooth. The fact that correction of the remainder of the arch does not have to wait for recovery of the impacted tooth and vice versa saves months to years in treatment time since anchorage is provided from a micropin and not the dental arch.

More specifically, the impacted tooth appliance includes a threaded micropin secured to the patient's bone, an apertured rigid ribbon secured to the impacted tooth by means of a rotatable bracket, a quadrilateral aperture formed in the micropin and a spring-biased quadrilateral wire inserted at one end through the quadrilateral aperture and secured at the other end to the apertured rigid ribbon. After the tooth is exposed, the bracket and wire are removed and a tube or similar device is bonded to the tooth. Following this, an angled quadrilateral wire and spring appliance is secured at one end to the tube and at the other end to the micropin.

DETAILED DESCRIPTION OF THE INVENTION

Figure 1:
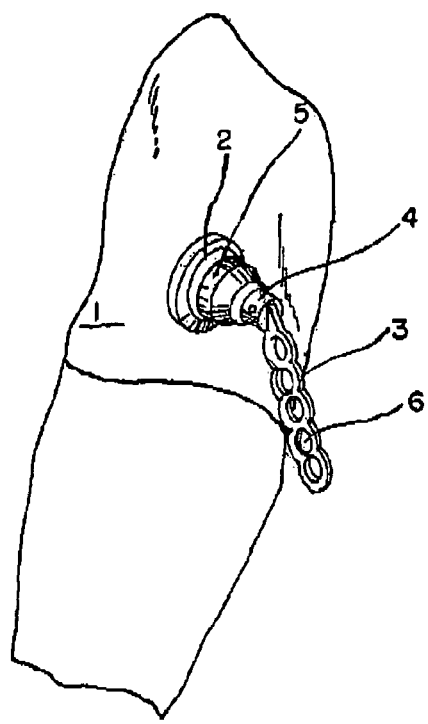
FIG. 1 is a perspective view of the tooth attachment means showing one feature of this invention.
Figure 2:
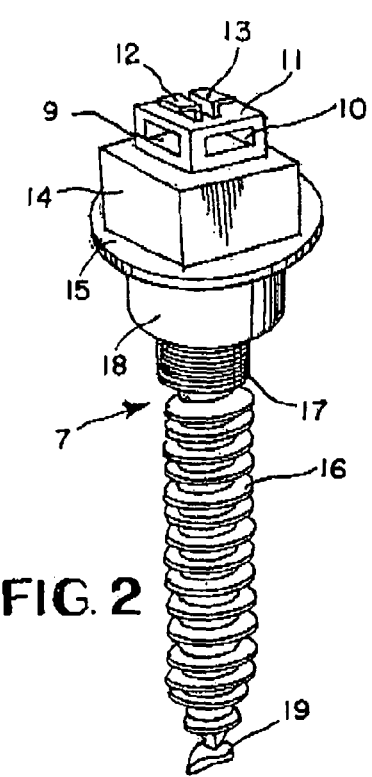
FIG. 2 is an enlarged perspective view of the micropin according to this invention.
Figure 3:
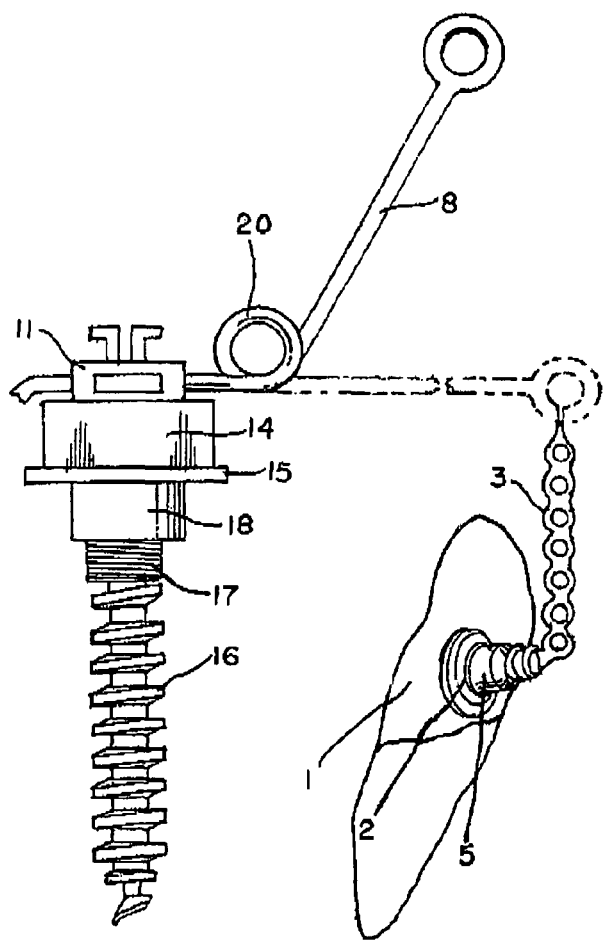
FIG. 3 is an enlarged elevational view of the complete appliance.

According to this invention, initially impacted tooth 1 is exposed by means of a surgical procedure. Then a bracket including bracket base 2 is initially is placed in position using a bracket holder or hemostat and bracket base 2 is bonded to tooth 1. Calibrated inflexible or rigid ribbon 3 is pivotally attached to bracket base 2 by means of pin 4 which is interlocked with respect to cone 5. Ribbon 3 is made of an alloy such as NiTi, elgiloy, TMA or stainless steel. Cone 5 is snap fastened into bracket base 2, in known manner, such that cone 5 rotates within bracket base 2. Both bracket base 2 and cone 5 are round in configuration. Since ribbon 3 is pivoted to cone 5 which in turn is rotatable 360 degrees, ribbon 3 is universally moveable to any desired position. The rigid nature of ribbon 3 helps achieve the desired directional force and delivers torque control and an efficient transfer of force to the impacted tooth. Additionally, ribbon 3 prevents undesirable floating of the impacted tooth. This is important because the surgical access and bonding of the impacted tooth can be challenging, especially when the tooth is deeply positioned in the palate.

Apertures 6, formed in ribbon 3, emerge into the oral cavity as the tooth descends and are calibrated to aid the clinician in determining the proximity of the crown of the tooth from the oral cavity as the tooth is force erupted. Multiple apertures 6 are of a diameter large enough to accept a ligature wire and the length of ribbon 3 is sufficient to span the distance from the position of the impacted tooth to the oral cavity which is 10 mm or longer.

A distinctive feature of this invention is the use of a Class III lever system instead of sliding mechanics i.e., gold chain, etc. Anchorage is provided by a micropin, generally designated by the numeral 7, using the cortical bone plate of the palate to stabilize the pin with the vector of force provided by rectangular spring wire 8. Wire 8 is prefabricated from NiTi, TMA or blue or yellow elgiloy types of orthodontic alloys.

Another feature of this invention is the ability to isolate and treat the impacted tooth independent of the rest of the arch. This is achieved using anchor micropin 7 instead of the dental arch as edgewise (rectangular or square) wire 8 is able to generate a vector of force that can be directed from a proximal point to deliver the desired movement at a distal location. For the purpose of receiving wire 8, quadrilateral apertures 9 and 10 are formed in block 11 and are disposed at a 90-degree angle to each other. Wire receiving hooks 12 and 13 extend from the upper surface of block 11. Quadrilateral apertures 9 and 10 are large enough to accept a 0.016×0.022 mm wire with minimal rotational play.

In order to receive a dental wrench, nut 14 is disposed between block 11 and disc 15. Also, micropin 7 includes two separate pairs of threads including conventional threads 16 and microthreads 17. Threads 16 and microthreads 17 extend downwardly from neck 18 of micropin 7 and microthreads 17 are provided for a more secure and immovable connection for micropin 7 to the cortical bone. Corkscrew-type tip 19 is formed on the end of micropin 7.

The orthodontic wire makes possible various types of orthodontic movements by providing three-dimensional control of the direction of the force provided. This is accomplished by virtue of micropin 7 providing a stable anchor unit so that the tooth is guided to the desired position due to the torque control made possible by the rectangular wire locked into either quadrilateral aperture 9 or 10 at its distal end.

Micropin 7 is placed near the midpalatine suture in the area of the first molar. Cortical bone is thickest in this area and provides better anchorage for the pin. Following this, spring 20 is formed in wire 8 and activated by bending it manually, so as to achieve the desired force, and then inserted into block 11 of the micropin. Spring 20 is loaded with 600-800 grams of force in order to deliver 150 grams of force to the impacted tooth and is formed by means of one or more coils in wire 8. The proximate end of wire 8 is tied to ribbon 3 positioned on the impacted tooth bracket using a 0.09 mm ligature wire.

The impacted tooth is brought down into the oral cavity normally within 4-12 weeks. As the tooth descends into the oral cavity, the extruding end of the ribbon can be adjusted for patient comfort during a routine office visit. The desired force is delivered to the impacted tooth to provide a light continuous and controlled force for optimal results and to minimize the risk of root resorption. The force is calibrated and controlled at all times during the treatment to deliver optimal force to the tooth for its movement.

The efficiency of the system is due to the Class III lever system. In Class III levers, the fulcrum is at one end of the lever (the micropin), but the load (the impacted tooth) is at the other end, and a force or effort is applied between the two (by a spring-loaded wire). The lever cannot give any mechanical advantage. The main advantage of Class III levers is the increased acceleration of movement of the tooth. Regardless of where the force is applied, the force must always be greater than the resistance of the load. However, the advantage is the speed and acceleration attained with this lever system. The longer the arm, the lower the amount of force needed to move the tooth. The components are assembled in a similar fashion to a door hinge to allow a 180-degree swivel in one dimension.

Figure 4:
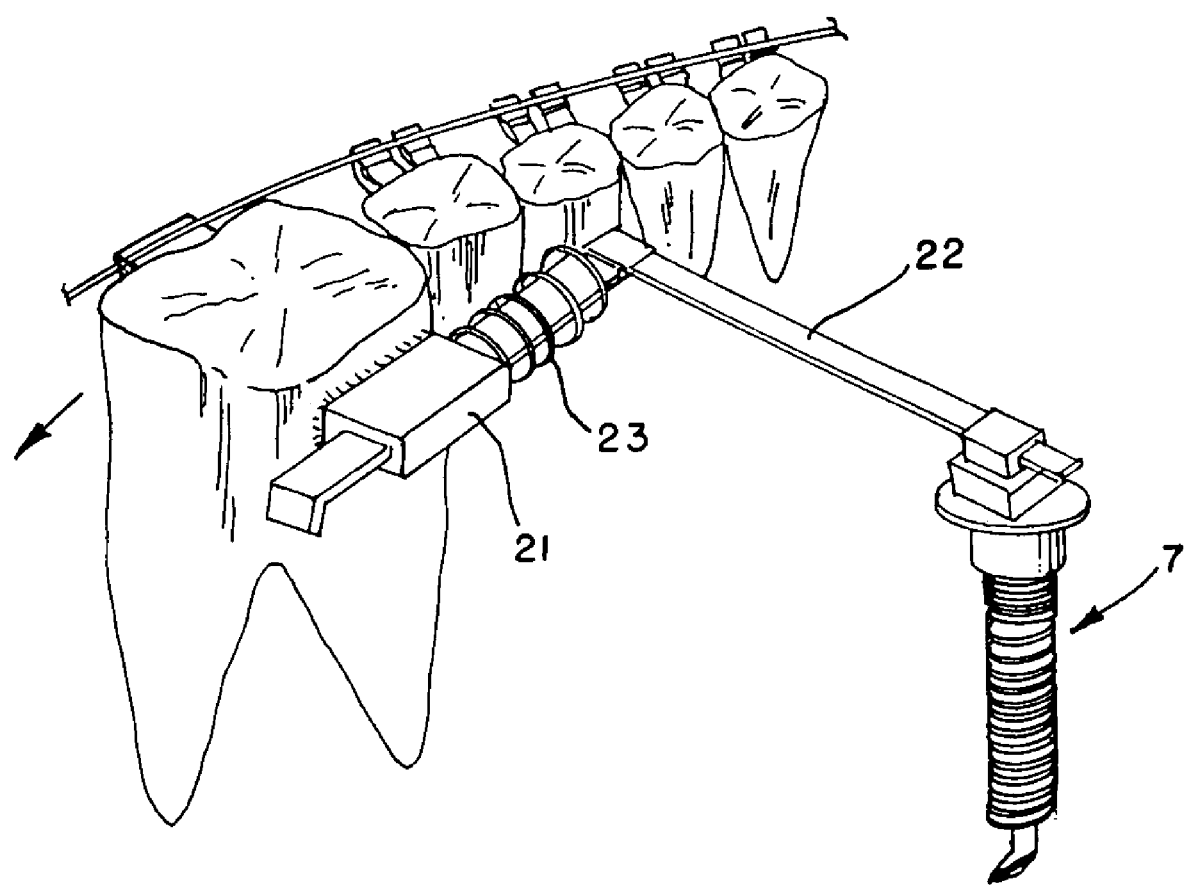
FIG. 4 is a perspective view of the micropin wire and tooth attachment assembly according to one feature of this invention and with the micropin shown as being enlarged.

Once the extrusion is complete and the crown of the tooth breaks through the oral mucosa, ribbon 3, bracket base 2 and related structure are removed and replaced with a bondable eyelet or tube 21, as shown in FIG. 4. This will allow movement of the tooth into the arch using a light and continuous force. This is vector force mechanics as opposed to sliding mechanics and this phase of the treatment is independent of the rest of the dental arch. The only requirement is for this movement to be orchestrated with the rest of the arch such that adequate space is available for the tooth at the desired location in the arch.

Following this, a new rectangular wire 22 and spring 23 assembly is inserted, at one end, into either aperture 9 or 10 of micropin 7 or into a new micropin placed in a better position for the forward movement of the palatially-positioned tooth and inserted into tube 21 at the other end in order to move the tooth forward toward the arch. Wire 22 is angled with spring compression 23 disposed between tube 21 and the converging point of the angled wire in order to exert tension on the tooth. Both ends of wire 22 are bent downwardly to prevent wire 22 from sliding out of micropin 7 or tube 21. Once the tooth arrives in the proximity of its final position, tube 21, micropin 7, wire 22 and spring 23 are removed and a conventional bracket is bonded to the tooth. The tooth is then treated along with the rest of the arch to correct the malocclusion.

Therefore, by this invention, an impacted tooth is lifted out of its deeply embedded position using a lever system. The impacted tooth is connected to the active arm of the lever with a rigid ribbon bracket and lifted out with the extrusion force generated from the lever arm. The lever arm is adjustable to control the amount of the force as well as the direction of the force delivered to the impacted tooth, as desired, including labial, lingual, or extrusive vectors as treatment demands. The correction of impacted tooth is independent from the remainder of the dental arch so that treatment of a separate malocclusion can be accomplished simultaneously.

The invention claimed is:

1. An orthodontic appliance for correcting an impacted tooth comprising
    a pin adapted to be anchored to bone,
    a bracket for being secured to said tooth,
    an elongated ribbon pivotally interconnected to said bracket,
    a block extending upwardly from said pin,
    a quadrilateral enclosed aperture formed in said block,
    a quadrilateral wire secured at one end to said ribbon and extending snugly through said quadrilateral enclosed aperture at the other end, and
    said bracket comprising a bracket base and a cone fastened to said bracket base and rotatable thereon.

2. An appliance according to claim 1 wherein said ribbon is rigid.

3. An appliance according to claim 1 wherein at least one aperture is formed in said ribbon and a ligature wire extends through one of said at least one aperture and is attached to said quadrilateral wire.

4. An appliance according to claim 1 wherein an adjustable coiled spring is formed in said quadrilateral wire intermediate said bracket and said pin.

5. An appliance according to claim 1 wherein a pair of quadrilateral enclosed apertures are formed in said block and are disposed 90 degrees to each other.

6. An appliance according to claim 1 wherein the lower portion of said pin is threaded, said pin comprises threads, and said threads comprise microtbreads disposed on the upper portion of said threaded portion.

7. An appliance according to claim 1 wherein said ribbon is connected to said cone by means of a pin and is pivoted in a plane which is in coincidence with the axis of said cone.

8. An appliance according to claim 1 wherein said bracket base and said cone are circular in configuration.

9. An orthodontic appliance for correcting an impacted tooth comprising
    a pin adapted to be anchored to bone,
    a bracket for being secured to said tooth,
    an elongated ribbon pivotally interconnected to said bracket,
    a block extending upwardly from said pin,
    a quadrilateral aperture formed in said block,
    a quadrilateral wire secured at one end to said ribbon and extending through said quadrilateral aperture at the other end, and
    said bracket comprising a bracket base and a cone fastened to said bracket base and rotatable thereon.

10. An appliance according to claim 9 wherein said ribbon is connected to said cone by means of a pin and is pivoted in a plane which is in coincidence with the axis of said cone.

11. An appliance according to claim 9 wherein said bracket base and said cone are circular in configuration.

12. An orthodontic appliance for correcting an impacted tooth using a Class III lever system comprising
    a pin adapted to be anchored to bone and acting as a fulcrum,
    said Class III lever system comprising a load and a force or effort,
    a bracket for being secured to said tooth such that said tooth acts as the load,
    an elongated rigid ribbon pivotally interconnected to said bracket,
    a block extending upwardly from said pin,
    a one-piece quadrilateral enclosed aperture intergrally formed through said block,
    a quadrilateral wire secured at one end to said ribbon and extending snugly through said quadrilateral enclosed aperture at the other end, and
    an adjustable spring formed in said quadrilateral wire such that said spring is intermediate said bracket and said pin during use and acts as the force or effort.

13. An appliance according to claim 12 wherein said spring is a coil spring.

* * * * *